(12) United States Patent
Buiser et al.

(10) Patent No.: US 8,398,696 B2
(45) Date of Patent: Mar. 19, 2013

(54) MICROCATHETER INTRODUCER SHEATH

(75) Inventors: Marcia Buiser, Marlborough, MA (US); Ashley Seehusen, Newton, MA (US); Christopher J. Elliott, Hopkinton, MA (US); Aidan O'Connor, Douglas (IE); Patrick G. O'Connor, Saint Joseph Road (IE); Mike Sheehy, Passage West (IE)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1249 days.

(21) Appl. No.: 12/038,516

(22) Filed: Feb. 27, 2008

(65) Prior Publication Data

US 2008/0234723 A1 Sep. 25, 2008

Related U.S. Application Data

(60) Provisional application No. 60/892,411, filed on Mar. 1, 2007.

(51) Int. Cl.
A61F 2/06 (2006.01)

(52) U.S. Cl. .................................... 623/1.11

(58) Field of Classification Search .................. 604/158, 604/525, 103.09, 60, 103.05, 103.06, 272, 604/523; 606/200, 157; 623/1.11; 128/831, 128/843
See application file for complete search history.

(56) References Cited

U.S. PATENT DOCUMENTS

| | | | | |
|---|---|---|---|---|
| 4,850,975 A | * | 7/1989 | Furukawa | 604/170.01 |
| 5,120,308 A | * | 6/1992 | Hess | 604/170.01 |
| 5,167,647 A | | 12/1992 | Wijkamp et al. | |
| 5,312,415 A | * | 5/1994 | Palermo | 606/108 |
| 5,397,310 A | | 3/1995 | Chu et al. | |
| 5,746,734 A | | 5/1998 | Dormandy, Jr. et al. | |
| 6,059,748 A | * | 5/2000 | Teirstein et al. | 604/510 |
| 6,074,407 A | * | 6/2000 | Levine et al. | 606/194 |
| 6,096,022 A | * | 8/2000 | Laymon et al. | 604/523 |
| 6,149,664 A | * | 11/2000 | Kurz | 606/194 |
| 6,398,791 B1 | * | 6/2002 | Que et al. | 606/127 |
| 2005/0004598 A1 | | 1/2005 | White, Jr. et al. | |
| 2005/0245963 A1 | | 11/2005 | Kida et al. | |
| 2006/0135981 A1 | | 6/2006 | Lenker et al. | |
| 2006/0282112 A1 | | 12/2006 | Griffin | |
| 2007/0141099 A1 | | 6/2007 | Buiser et al. | |
| 2007/0142859 A1 | | 6/2007 | Buiser et al. | |
| 2007/0142893 A1 | | 6/2007 | Buiser et al. | |

FOREIGN PATENT DOCUMENTS

WO  WO 2005/107612 A1  11/2005

OTHER PUBLICATIONS

Boston Scientific Corp., "Interlock™ Fibered IDC Occlusion System" (Brochure), 2006.
International Search Report for International Application No. PCT/US2008/055065 mailed Jun. 19, 2008.
Written Opinion of the International Searching Authority for International Application No. PCT/US2008/055065 mailed Jun. 19, 2008.

* cited by examiner

*Primary Examiner* — Gary Jackson
*Assistant Examiner* — Jonathan Hollm
(74) *Attorney, Agent, or Firm* — Seager, Tufte & Wickhem LLC

(57) ABSTRACT

The present invention includes an introducer sheath. The sheath may comprise a first proximal elongated section having a first outer diameter and a first inner diameter, and a main body elongated section having a second inner diameter and a second outer diameter, wherein the second outer diameter is larger than the first outer diameter. The sheath may further include a distal section having an outer wall that tapers from the second outer diameter of the main body elongated section to a smaller distal outer diameter.

18 Claims, 3 Drawing Sheets

MICROCATHETER INTRODUCER SHEATH

This application claims the benefit of U.S. Provisional Application Ser. No. 60/892,411, filed Mar. 1, 2007, which is incorporated herein by reference in its entirety.

TECHNICAL FIELD

The present invention relates to the field of catheters, and more particularly, to introducer sheaths for use with vascular catheters.

BACKGROUND

Embolic coils can be used to treat a number of medical conditions. For example, embolic coils may be used to stop undesired blood flow or to treat vascular malformations or structural defects, as in, for example, the treatment of aneurysms, arteriovenous malformations, and/or traumatic fistulae. In addition, embolic coils can be used to reduce or stop the blood flow to tissues or organs to treat conditions such as tumors or hemorrhages.

Embolic coils are typically introduced into a blood vessel by using a microcatheter that extends from a proximal point outside the patient's body to a distal point near the embolization site. An introducer sheath containing the coil can be used to carry and protect the coil prior to insertion into the patient. Further, the introducer sheath may be used to transfer the coil to the microcatheter and/or to assist in deploying the coil at a selected embolization site.

However, some introducer sheaths are not optimized for successful coil delivery. For example, many sheaths are straight extrusions having a diameter sized to mate with the proximal hub of a microcatheter. Consequently, in order to match the small dimensions of microcatheters, many sheaths have thin walls that can buckle easily under compression, which can lead to premature detachment of the coils and/or make it difficult to advance the coil from the introducer sheath into the microcatheter. If this occurs, the physician may need to remove the microcatheter, potentially wasting time spent in securing access to the selected embolization site.

In addition, retrograde blood flow into the sheath can be a problem. For example, blood flow into the introducer sheath can cause premature thrombosis of some embolic coils, thereby preventing delivery into the microcatheter.

The present disclosure is directed at overcoming one or more of the short-comings of introducer sheaths as set forth above.

SUMMARY

A first aspect of the present invention includes an introducer sheath. The sheath may comprise a first proximal elongated section having a first outer diameter and a first inner diameter, and a main body elongated section having a second inner diameter and a second outer diameter, wherein the second outer diameter is larger than the first outer diameter. The sheath may further include a distal section having an outer wall that tapers from the second outer diameter of the main body elongated section to a smaller distal outer diameter.

A second aspect of the present invention includes a microcatheter system. The system may comprise a microcatheter. The introducer sheath may include a first proximal elongated section having a first outer diameter and a first inner diameter, and a main body elongated section having a second inner diameter and a second outer diameter, wherein the second outer diameter is larger than the first outer diameter. The sheath may further include a distal section having an outer wall that tapers from the second outer diameter of the main body elongated section to a smaller distal outer diameter.

A third aspect of the present invention includes a method of delivering an embolic coil through a microcatheter. The method may include providing a microcatheter. The method may further include selecting an introducer sheath including a first proximal elongated section having a first outer diameter and a first inner diameter, and a main body elongated section having a second inner diameter and a second outer diameter, wherein the second outer diameter is larger than the first outer diameter. The sheath may further include a distal section having an outer wall that tapers inward from the second outer diameter of the main body elongated section to a smaller distal outer diameter. The method may further include inserting the distal section having an outer wall that tapers inward into the microcatheter and advancing the introducer sheath to a predetermined location within the microcatheter.

A fourth aspect of the present disclosure includes an introducer sheath. The sheath may comprise a first proximal elongated section having a first outer diameter and a first inner diameter, and a main body elongated section having a second inner diameter and a second outer diameter, wherein the second outer diameter is approximately equal to the first outer diameter. The sheath may further include an intermediate section disposed between the proximal section and main body section and having an outer diameter that is smaller than both the first outer diameter and second outer diameter, and a distal section having an outer wall that tapers from the second outer diameter of the main body elongated section to a smaller distal outer diameter.

Additional aspects and advantages of the invention will be set forth in part in the description which follows, and in part will be apparent from the description, or can be learned by practice of the invention. The advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate several embodiments of the invention and together with the description, serve to explain the principles of the invention.

DESCRIPTION OF THE EMBODIMENTS

Reference will now be made in detail to the exemplary embodiments of the invention, examples of which are illustrated in the accompanying drawings. Wherever possible, the same reference numbers will be used throughout the drawings to refer to the same or like parts.

Figure 1A:
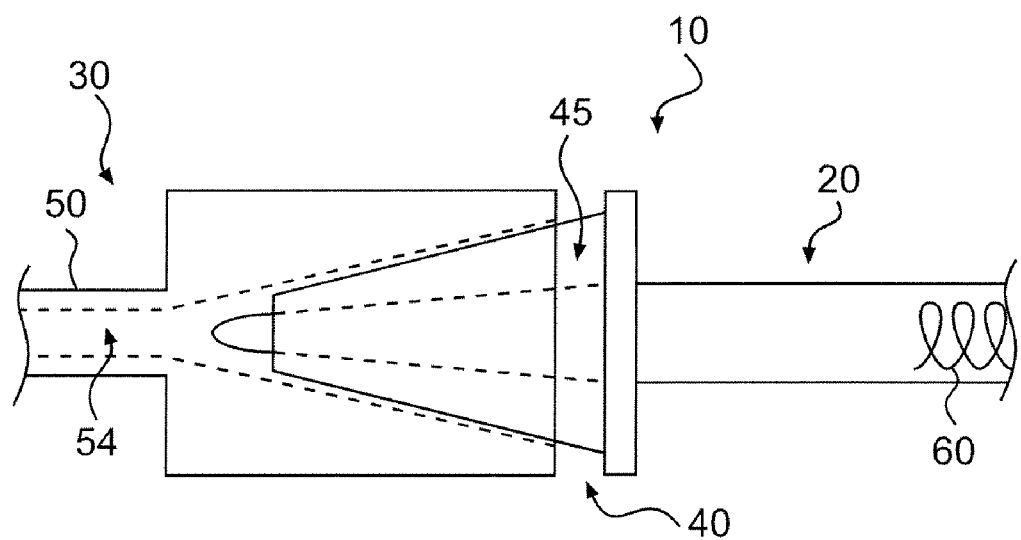
FIG. 1A illustrates a side view of an embolic coil delivery system, including an introducer sheath, according to an exemplary embodiment.

FIG. 1A illustrates a perspective view of an embolic coil delivery system 10, including an introducer sheath 20, according to an exemplary embodiment. As shown, the system 10 includes a microcatheter 30, including a catheter hub 40, configured to receive introducer sheath 20. The microcatheter 30 further includes an elongated body 50, having a lumen 54 which, when inserted into a vascular structure (e.g. a vein or artery), extends into a patient's body to a desired delivery site.

As shown, the microcatheter 30 and catheter hub 40 include a introducer stabilizer 45, which can facilitate insertion of the sheath 20 into the microcatheter 30. An exemplary embodiment of a catheter hub with a stabilizer 45 is described in U.S. Patent Publication, 2005/0245963, to Kida et al., which published on Nov. 3, 2005 and is herein incorporated by reference in its entirety. However, it should be noted that any suitable catheter and hub assembly as is known in the art may be used with the introducer sheath of the present disclosure.

Figure 1B:
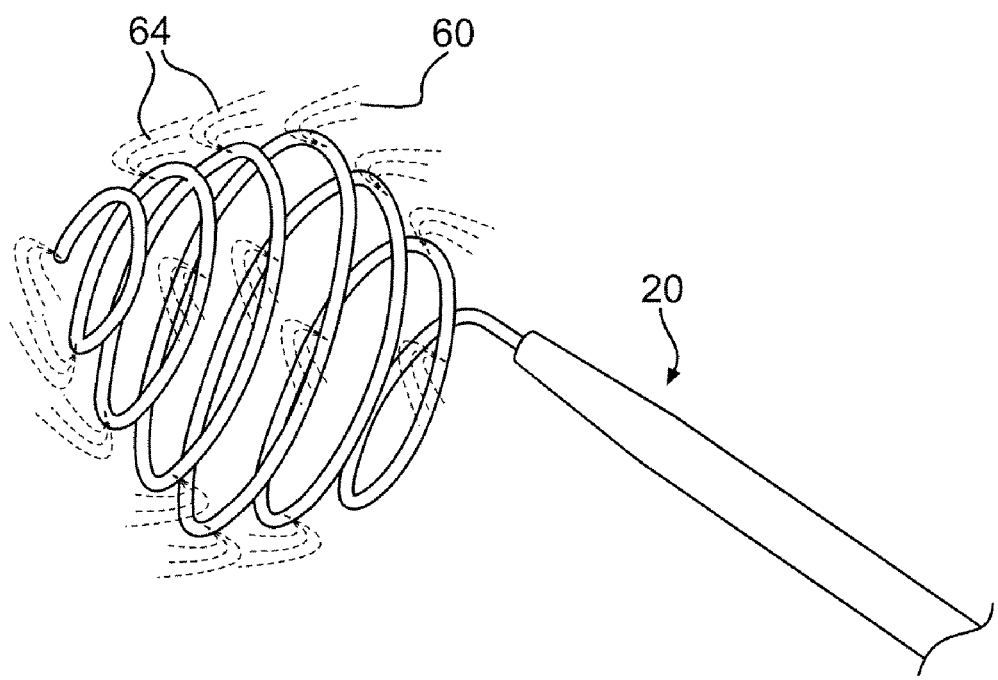
FIG. 1B illustrates an introducer sheath and embolic coil, according to an exemplary embodiment.

FIG. 1B illustrates an enlarged, more detailed view of the introducer sheath 20, along with an embolic coil 60 that may be delivered through a microcatheter 30 using the introducer sheath 20. As shown, the coil 60 is extended from the inner lumen of the sheath 20. However, during typical use, before the coil 60 is released, a microcatheter 10 will be advanced to an anatomical site where the coil is to be implanted. Next, the introducer sheath 20 will be inserted into the lumen of the microcatheter 30 through a hub 40. The physician will then generally ensure that the catheter 30 and sheath 20 are appropriately positioned with respect to a desired delivery site, (e.g. using fluoroscopy or other suitable localization method), and the coil 60 will be released from the sheath 20 and advanced to the appropriate anatomic site.

The coil 60 may be secured within the sheath 20 prior to delivery using a number of suitable methods. For example, the coil 60 can include a mechanical attachment and releasing system (not shown), whereby the coil 60 is mechanically connected and released from a guide wire controlled by a physician. For example, suitable mechanical attachments between embolic coils and pusher wires are described in U.S. Pat. No. 5,925,059, which issued to Palermo on Jul. 20, 1999, and is herein incorporated by reference in its entirety. However, any suitable release mechanism may be used. For example, various release mechanisms known in the art include other mechanical, electrolytic, chemical, and magnetic attachment and release mechanisms.

In addition, a variety of suitable embolic coils may be selected. For example, generally, the coil 60 will include a relatively biologically-inert and compatible material such as platinum. However, any suitable material may be selected as long as the coil is biologically compatible and has properties suitable for accomplishing a desired clinical outcome (e.g. stopping blood flow, delivering a therapeutic, etc.). Further, some coils may include surface features selected to enhance desired features. For example, as shown, the coil 60 includes fibers 64 selected to promote thrombosis, thereby ensuring suitable clotting and control of blood flow. However, other suitable coils may include drug-delivery systems, markers for use with radiological visualization or localization systems, drugs to prevent or promote coagulation or platelet aggregation, and/or drugs selected for other suitable therapeutic goals.

In addition, it should be noted that although the introducer sheath 20 and microcatheter system 10 are described for use with embolic coils, the sheath 20 and system 10 may be used for other therapeutic or diagnostic purposes without the use of coils. For example, the sheath 20 and system 10 may be used to facilitate delivery of any other therapeutic device or drug, including, for example, stents, sensors, filters, and/or other types of occlusion systems to control blood flow.

Figure 2A:
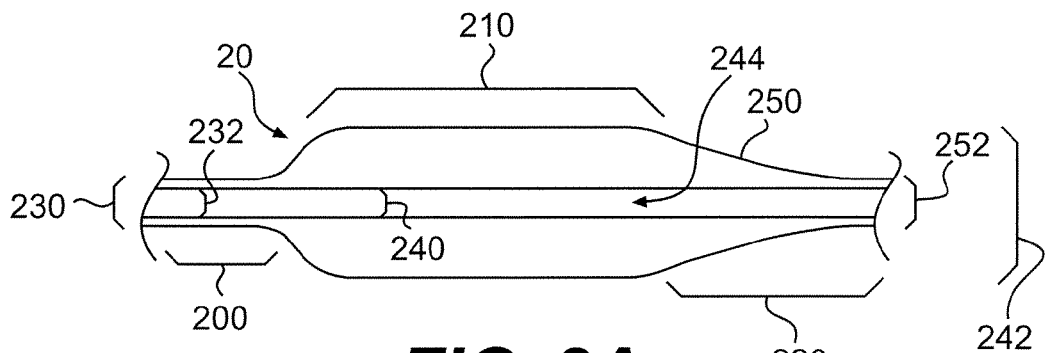
FIG. 2A illustrates a side view of an introducer sheath, according to an exemplary embodiment.

FIG. 2A illustrates a side view of an introducer sheath 20, according to an exemplary embodiment. As shown, the introducer sheath 20 includes a first proximal elongated section 200 having a first outer diameter 230 and a first inner diameter 232. The sheath 20 further includes a main body elongated section 210 having a second inner diameter 240 and a second outer diameter 242, wherein the second outer diameter 242 is larger than the first outer diameter 230. Further, the sheath 20 includes a distal section 220 having an outer wall 250 that tapers from the second outer diameter 242 of the main body elongated section 210 to a smaller distal outer diameter 252. As shown in FIG. 2A, the first inner diameter 232 of the proximal elongated section 200 may be approximately equal to the second inner diameter 240 of the main body section 210, but in other embodiments, the first inner diameter 232 may be greater than the second inner diameter 240, as described below.

As shown, the proximal section 232 is contemplated to be the section of the sheath 20 that is nearest the physician or operator while the device is inserted into a microcatheter hub. Further, the distal section 220 is contemplated to be the portion of the sheath that is first advanced into a microcatheter hub towards a site for deployment of an embolic coil. In addition, the distal section 220 can include a distal opening through which a coil or other treatment device may be released into a microcatheter for treatment of a patient.

It should be noted that, as shown, the relative dimensions of the proximal section 200, main body section 210, and distal section 220 are drawn to explain the features of the sheath 20. However, the actual dimensions of a sheath used to treat a patient may vary significantly. For example, typically, a sheath 20 may have an overall length of about 80 to about 100 cm, and more typically about 95 cm. Further, the proximal section 200 may be between about 15 cm and about 25 cm in length, while the distal section (i.e. starting where the wall 250 tapers and ending at the sheath opening) may be between about 1 cm and about 2 cm in length. Further, typical diameters may vary. For example, the main body outer diameter 242 will typically be between about 0.05 inches and about 0.07 inches, while the main body inner diameter 240 will typically be between about 0.01 inches and about 0.03 inches, between about 0.03 inches and about 0.05 inches for larger coils, or between about 0.02 inches and about 0.04 inches for intermediate sized coils. However, the specific sheath length and diameters may be selected based on the anatomic site to be treated, the material used to produce the sheath, and/or the type of coil or other device to be delivered by the sheath.

In some embodiments, the inner diameter 240 of the main body section 210 may be selected to improve pushability of a coil through a lumen 244 of the sheath 20. For example, it may be desirable to select an inner diameter 240 and a coil size such that the size difference between the lumen 244 and coil is less than a maximum value. Maintaining this size difference below a certain value may reduce coil kinking or bending, and improve coil column strength and pushability. For example, in some embodiments, the inner diameter 240 and coil size may be selected to produce a difference in the lumen and coil cross-sectional areas that is less than a predetermined value. For example, for a coil having a diameter of about 0.011 inches and a main body inner diameter of about 0.021 inches, the difference in cross-sectional areas is approximately 73% (as expressed as a percent of the lumen cross-sectional area).

It should be noted that the lumen and coil cross-sections, as described above, will generally be approximately cylindrical. However, it is contemplated that other configurations may be used. For example, lumen cross-sections may also have oval shapes, square shapes, or any other suitable configuration. In addition, as shown, the sheath proximal section 200, main body 210, and distal section 220 are contiguous. However, it is contemplated that additional sections, including additional narrowing sections or widened sections of the sheath 21, may be disposed between one or more of the proximal section 200, main body 210, and distal section 220.

Figure 2B:
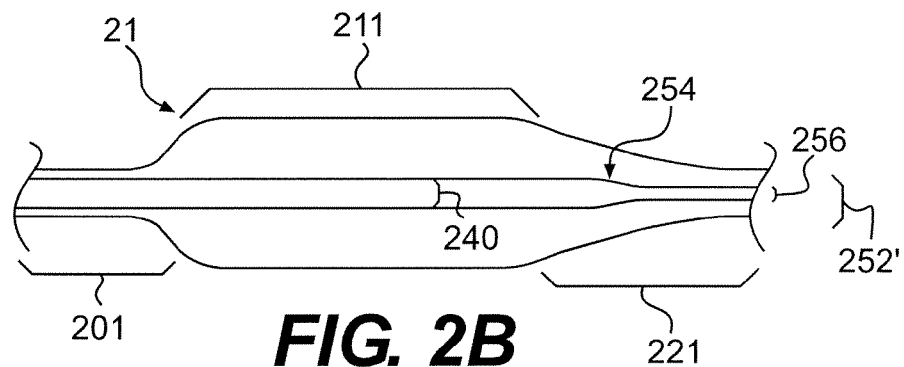
FIG. 2B illustrates a side view of an introducer sheath, according to another exemplary embodiment.

FIG. 2B illustrates a side view of an introducer sheath 21, according to another exemplary embodiment. Again, the sheath 21 includes a proximal section 201, a main body portion 211, and a distal section 221. As shown in this embodiment, the inner diameter 240 of the main body section may include an inward taper 254 near the distal section 221 so that the distal section 221 includes an inner diameter 256 that is smaller than the second inner diameter 240 of the main body elongated section. The smaller inner diameter 256 at distal section 221 may reduce retrograde blood flow into sheath 21, thereby preventing premature clotting on a coil or other device contained within sheath 21.

It should be noted that the inner diameter 256 of the distal section 221 may be selected to allow a coil to be deployed through an opening in distal section 221. However, the inner diameter 256 may further be made as small as possible while allowing delivery of a coil and minimizing retrograde blood flow. For example, for a sheath having a main body outer diameter of about 0.060 inches, the inner diameter 256 of the distal section 221 may be between about 0.024 inches to about 0.026 inches, and the distal section outer diameter 252' may be between about 0.017 inches and 0.019 inches, but other suitable dimensions may be selected. Further, although as shown, the sheath 21 includes an inward taper 254 to produce a wider main body inner diameter 240 and narrower distal inner diameter 256, the sheath 21 may alternatively include a stepped configuration, whereby there is a more abrupt change in diameter from the main body section 211 and distal section 221.

Figure 2C:
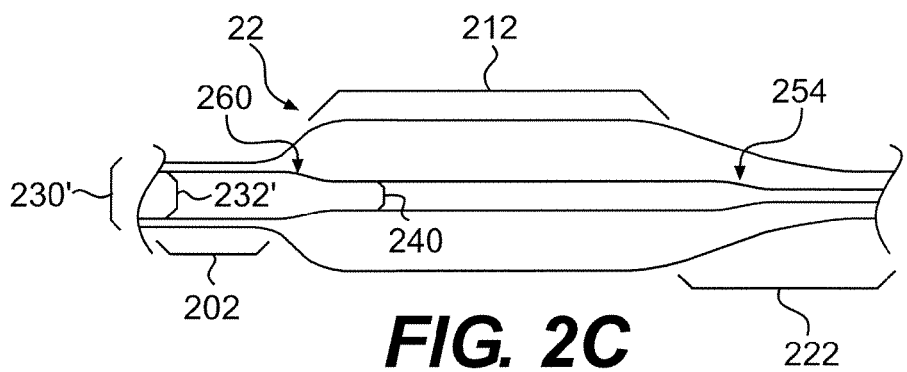
FIG. 2C illustrates a side view of an introducer sheath, according to another exemplary embodiment.

FIG. 2C illustrates a side view of an introducer sheath, according to another exemplary embodiment. As shown, the sheath 22 again includes a proximal section 202, a main body portion 212, and a distal section 222. However, in this embodiment, the sheath proximal section 202 includes a first inner diameter 232' that is larger than the second inner diameter 240 of the sheath main body section 240. Further, in some embodiments, the inner diameter of the main body section 240 may include a tapered region 260, whereby the inner diameter of the main body section enlarges to match the inner diameter 232' of the proximal section 202.

The larger inner diameter 232' of the proximal section may provide manufacturing advantages. For example, for some sheath designs, the sheath is secured to a guide wire during shipping and storage. In some cases, the sheath may be secured to the guide wire by heating a portion of the sheath and twisting that portion of the sheath to lock the sheath to the guide wire. (This may also be done while the sheath is still hot after an extrusion or other manufacturing process). When the physician is ready to use the device, the physician can simply twist the sheath section in the other direction to unlock the guide wire.

The proximal section, having a narrower outer diameter than the main body and/or a wider inner diameter, may facilitate this step of securing the sheath to the guide wire. In some cases, it may be desirable to have a relatively narrow sheath wall at the region of the sheath where the sheath will be heated and twisted to secure to a guide wire. Therefore, the narrow outer diameter, and/or wider inner diameter, of the sheath proximal section will produce a thinner sheath wall that may be more easily heated and twisted to lock to a guide wire. For example, typical dimensions for the sheath proximal section may include an outer diameter 230, 230' between about 0.030 inches and 0.038 (for a device with a main body outer diameter 242 of about 0.060 inches), and an inner diameter 232, 232' between about 0.01 inches and about 0.03 inches. As an example, a suitable device may include a main body inner diameter of about 0.021 inches, a main body outer diameter of about 0.060 inches, a proximal section inner diameter of about 0.025 inches, a proximal section outer diameter (at the most distal portion of the device with the narrowest diameter) of about 0.034 inches, a distal section outer diameter of about 0.025 inches, and a distal section inner diameter of about 0.018 inches.

Figure 3:
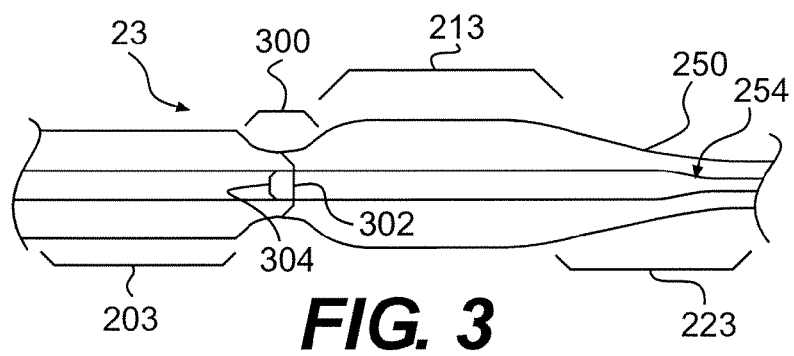
FIG. 3 illustrates a side view of an introducer sheath, according to yet another exemplary embodiment.
Figure 4:
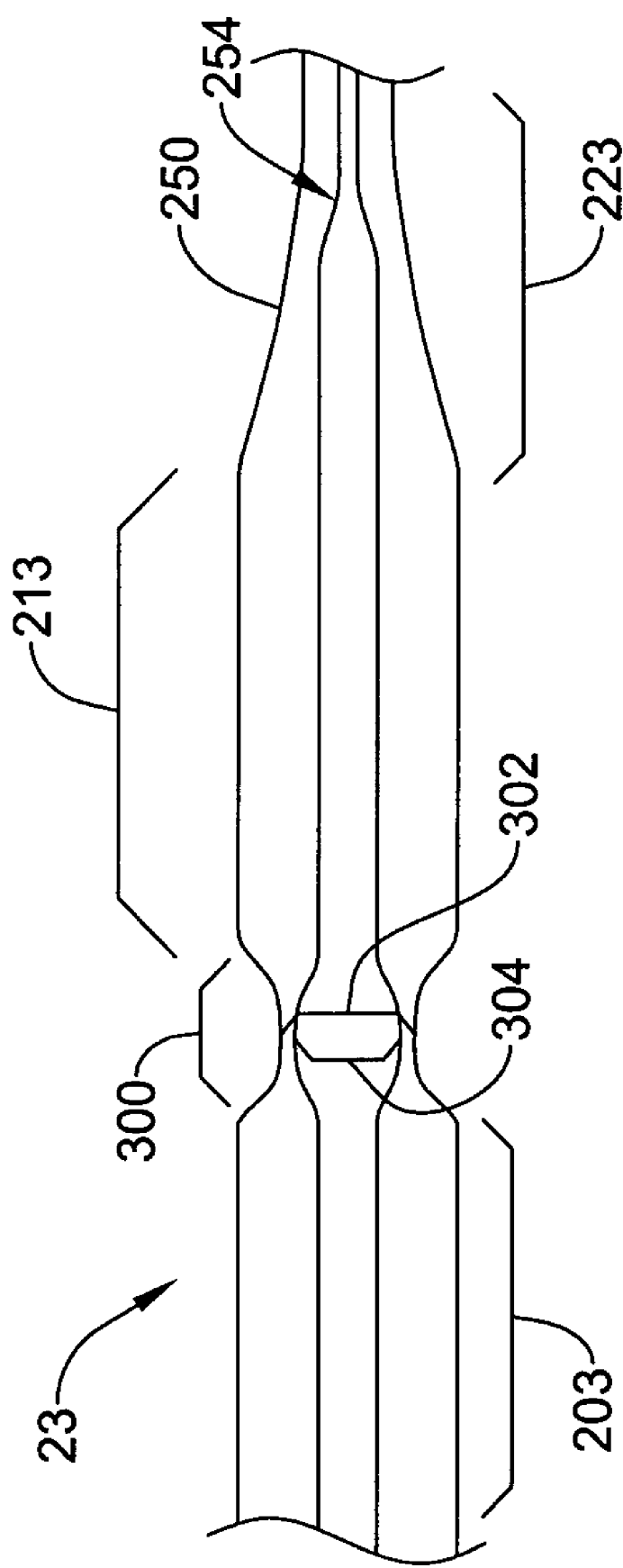
FIG. 4 illustrates a side view of an introducer sheath, according to still yet another exemplary embodiment.

FIG. 3 illustrates a side view of an introducer sheath, according to yet another exemplary embodiment. As shown, the sheath 23 again includes a proximal section 203, a main body portion 213, and a distal section 223. However, in this embodiment, the proximal section outer diameter is approximately equal to the main body outer diameter. Further, the sheath 23 includes a narrowed region 300 disposed between the proximal section 203 and main body section 213 having an outer diameter 302 that is smaller than the outer diameter of the proximal section 203 and main body section 213. Additionally, as shown, the narrowed region 300 includes an inner diameter 304 that is approximately equal to the inner diameters of the proximal section 203 and main body section 213. However, as illustrated in FIG. 4, the narrowed region inner diameter 304 can be larger than the inner diameter of the proximal section 203 and/or the main body section 213 to produce an even thinner sheath wall at the narrowed region 300.

As described above, the narrowed region 300 can include a wall thickness that is relatively thin. This may facilitate heating and twisting of the sheath wall at the narrowed region 300, thereby allowing the sheath 23 to be locked to and unlocked from a guide wire to facilitate shipment, storage, and subsequent use by a physician. For example, the narrowed region 300 may include inner and outer diameters similar to those described for proximal section outer and inner diameters 230' and 232' with respect to FIG. 2C. Further, the narrowed region 300 may have a range of lengths, including for example between about 1 cm and about 5 cm.

Suitable sheaths may be produced from a variety of materials and using a number of suitable manufacturing processes. For example, suitable sheaths may be produced using a number of thermoplastic extrusion processes and using a variety of materials, such as high-density or low-density polypropylene, polytetrafluoroethylene, and polyurethanes. Further, some sheaths may include two or more layers of materials, and/or material properties that vary along the sheath length. For example, when multiple layers are used, one layer may comprise an inner lubricious layer to ease the passage of coils, an anti-thrombogenic layer to prevent premature coil thrombosis, a hydrophilic inner layer to counteract increased friction due to thrombosis, and/or a tack outer layer to facilitate gripping. In addition, for sheaths having properties that vary along the length of the sheath, interrupted-layer co-extrusion or similar technologies may be used to produce differing materials along the length of the sheath. For example, sheaths may include extrusions at the distal end having a stiffness that will facilitate tactile confirmation of sheath connection to a catheter hub and/or higher resistance to deformation if excessive seating force is used. Further, sheaths may have a proximal extrusion having material properties that are amenable to twisting to lock and unlock a guide-wire.

Exemplary embodiments of the present invention have been described above. Those skilled in the art will understand, however, that changes and modifications may be made to these embodiments without departing from the true scope and spirit of the invention, which is defined by the claims.

LISTS OF ELEMENTS 10 microcatheter system
20 introducer sheath
21 introducer sheath (second embodiment)
22 introducer sheath (third embodiment)
23 introducer sheath (fourth embodiment)
30 catheter
40 catheter hub
45 stabilizer
50 catheter elongated section
54 catheter lumen
60 embolic coil
64 coil fibers
200 sheath proximal section
201 sheath proximal section
202 sheath proximal section
203 sheath proximal section
210 sheath main body section
211 sheath main body section
212 sheath main body section
213 sheath main body section
220 sheath distal section
221 sheath distal section
222 sheath distal section
223 sheath distal section
230 proximal section outer diameter
230' proximal section outer diameter
232 proximal section inner diameter
232' proximal section inner diameter
240 main body section inner diameter
242 main body section outer diameter
244 main body lumen
250 distal section tapered outer wall
252 distal section outer diameter
252' distal section outer diameter
254 distal taper
256 distal section inner diameter
260 proximal taper
300 narrow region
302 narrow outer diameter
304 narrow region inner diameter

The invention claimed is:

1. An introducer sheath, comprising:
a first proximal elongated section having a first outer diameter and a first inner diameter;
a main body elongated section having a second inner diameter and a second outer diameter each defined by a non-expandable wall thickness of the sheath, wherein the second outer diameter is larger than the first outer diameter and wherein the second inner diameter is smaller than the first inner diameter; and
a distal section having an outer wall that tapers from the second outer diameter of the main body elongated section to a smaller distal outer diameter.

2. The introducer sheath of claim 1, wherein the distal section further includes an inner diameter that is smaller than the second inner diameter of the main body elongated section.

3. The introducer sheath of claim 1, wherein the sheath includes a thermoplastic elastomer.

4. The introducer sheath of claim 3, wherein the thermoplastic elastomer is selected from the group consisting of polypropylene and polytetrafluroethyelene.

5. A microcatheter system, comprising:
a microcatheter; and
an introducer sheath, comprising:
a first proximal elongated section having a first outer diameter and a first inner diameter;
a main body elongated section having a second inner diameter and a second outer diameter each defined by a non-expandable wall thickness of the sheath, wherein the second outer diameter is larger than the first outer diameter and wherein the second inner diameter is smaller than the first inner diameter; and
a distal section having an outer wall that tapers from the second outer diameter of the main body elongated section to a smaller distal outer diameter.

6. The system of claim 5, wherein the distal section further includes an inner diameter that is smaller than the second inner diameter of the main body elongated section.

7. The system of any of claims 5, wherein the sheath includes a thermoplastic elastomer.

8. The system of claim 7, wherein the thermoplastic elastomer is selected from the group consisting of polypropylene and polytetrafluroethyelene.

9. The system of claim 5, further including a coil for delivery through the sheath and microcatheter.

10. The system of claim 9, wherein the main body inner diameter and coil are selected such that a difference between a cross-sectional area of the main body lumen and a cross-sectional area of the coil is less than 75%.

11. A method of delivering an embolic coil through a microcatheter, comprising:
providing a microcatheter;
selecting an introducer sheath, including:
a first proximal elongated section having a first outer diameter and a first inner diameter;
a main body elongated section having a second inner diameter and a second outer diameter each defined by a non-expandable wall thickness of the sheath, wherein the second outer diameter is larger than the first outer diameter and wherein the second inner diameter is smaller than the first inner diameter; and
a distal section having an outer wall that tapers from the second outer diameter of the main body elongated section to a smaller distal outer diameter;
inserting the distal section having an outer wall that tapers inward into the microcatheter; and
advancing the introducer sheath to a predetermined location within the microcatheter.

12. The method of claim 11, wherein the distal section further includes an inner diameter that is smaller than the second inner diameter of the main body elongated section.

13. The method of claim 11, wherein the sheath includes a thermoplastic elastomer.

14. The method of claim 13, wherein the thermoplastic elastomer is selected from the group consisting of polypropylene and polytetrafluroethyelene.

15. An introducer sheath, comprising:
a first proximal elongated section having a first outer diameter and a first inner diameter;

a main body elongated section having a second inner diameter and a second outer diameter, wherein the second outer diameter is approximately equal to the first outer diameter;

an intermediate section disposed between the proximal section and the main body section and having an outer diameter that is smaller than both the first outer diameter and the second outer diameter and an inner diameter that is greater than the second inner diameter; and a distal section having an outer wall that tapers from the second outer diameter of the main body elongated section to a smaller distal outer diameter.

16. The introducer sheath of claim 15, wherein the distal section further includes an inner diameter that is smaller than the second inner diameter of the main body elongated section.

17. The introducer sheath of any of claims 15, wherein the sheath includes a thermoplastic elastomer.

18. The introducer sheath of claim 17, wherein the thermoplastic elastomer is selected from the group consisting of polypropylene and polytetrafluroethyelene.

* * * * *